United States Patent [19]
Forberg

[11] Patent Number: 5,234,412
[45] Date of Patent: Aug. 10, 1993

[54] FLOW REGULATOR FOR A DRIP CHAMBER

[76] Inventor: Hans-Jürgen Forberg, Sebenter Weg 4, D-2432 Damlos, Fed. Rep. of Germany

[21] Appl. No.: 761,931
[22] PCT Filed: Jan. 22, 1991
[86] PCT No.: PCT/DE91/00066
  § 371 Date: Sep. 16, 1991
  § 102(e) Date: Sep. 16, 1991
[87] PCT Pub. No.: WO91/11211
  PCT Pub. Date: Aug. 8, 1991

[30] Foreign Application Priority Data
  Jan. 25, 1990 [DE] Fed. Rep. of Germany ....... 4002089

[51] Int. Cl.⁵ .................................................. A61M 5/00
[52] U.S. Cl. ................................. 604/248; 604/250; 604/251; 251/9
[58] Field of Search ............... 604/246, 248, 250, 251; 251/4, 9, 251, 340

[56] References Cited

U.S. PATENT DOCUMENTS

| | | | |
|---|---|---|---|
| 2,825,333 | 3/1958 | Broman | 251/9 |
| 3,612,474 | 10/1971 | Strohl | 251/9 |
| 3,880,401 | 3/1975 | Wiltse | 604/248 |
| 4,176,683 | 12/1979 | Leibinsohn | 251/4 |
| 4,378,013 | 3/1983 | LeFevre | 604/250 |
| 4,609,300 | 10/1986 | Robert | 251/9 |
| 4,687,176 | 8/1987 | Olsen | 251/9 |

FOREIGN PATENT DOCUMENTS

| | | |
|---|---|---|
| 2452117 | 5/1976 | Fed. Rep. of Germany . |
| 2725429 | 6/1977 | Fed. Rep. of Germany . |
| 3044572 | 11/1980 | Fed. Rep. of Germany . |
| 3146541 | 11/1981 | Fed. Rep. of Germany . |
| 2745317 | 8/1987 | Fed. Rep. of Germany . |
| 2221151 | 10/1974 | France ................................. 604/248 |

*Primary Examiner*—John D. Yasko
*Assistant Examiner*—Anthony Gutowski
*Attorney, Agent, or Firm*—Dvorak and Traub

[57] ABSTRACT

A device for infusion or transfusion can be connected to a flexible tube line (16). The regulating arrangement (8, 9, 10, 12) for regulating the flow rate of the fluid through the flexible tube line (16) is a rigid structural member of the intravenous drip chamber (1) containing the infusion or transfusion liquid. The flow rate is regulated by means of a regulating nut (12) which effectively connects the regulating knob (10) with a flexible tube line (16). The structural member has a tubular connection piece (2) provided with a closed end (3) and having lateral perforations (4). The tubular connection piece (2) is coaxially spaced by a surrounding tubular threaded pipe (6) divided into segments (8, 9) separated by dividing points (7). The lateral perforations (4) open into downwardly directed grooves (5) which establish a flow path. The segments (8, 9) are provided with regulating members (10) which move the tube line into the grooves (5) and are displaceable by an internally threaded regulating nut (12) threaded on the threaded pipe (6).

6 Claims, 1 Drawing Sheet

FLOW REGULATOR FOR A DRIP CHAMBER

BACKGROUND OF THE INVENTION

1. Field of the Invention

The invention relates to a device which is able to be used in particular as a medical infusion- or transfusion instrument, with a drip chamber, containing a fluid, for a tube lien and with an arrangement for regulating the quantity of fluid flowing through the tube line.

2. Description of Prior Art

In such devices, arrangements are used for regulating the through flow quantity which are suited to alter the through flow cross-section of the tube line in an adjustable manner. Such arrangements are usually applied on the tube line and, as can be seen for example from the DE-OS 2 242 539, are constructed as a so-called roller clamp or bring about the regulation of the through flow cross-section according to a different principle by means of a cam which is able to be adjusted by means of levers, as disclosed for example by the U.S. Pat. No. 4,697,785.

In practical use, however, it has been found that the proper function of the known arrangements is affected by the elasticity of the tube line and its diameter- and wall thickness tolerance. The foregoing has an influence on the constancy of the through flow rate. In addition, it is a disadvantage in the known arrangements that their application on the tube is relatively complicated and time-consuming.

SUMMARY OF THE INVENTION

The object of the invention consists in improving the device indicated in the introduction to the effect that a simplified and easily assembled regulating arrangement is proposed, whereby the through flow rate can be kept constant in a reliable manner independently of the the tube parameters. Furthermore, the manufacturing expenditure for such an arrangement is to be minimized.

This problem is solved according to the invention in that the regulating arrangement is a fixed component of the drip chamber.

A preferred form of an embodiment consists in that the drip chamber is provided on its lower part with a connection piece serving to attach the tube line. Such connection piece is constructed so as to be closed at its front end and is equipped with at least one radial perforation, which in each case opens out into a longitudinal groove. The perforations are towards the front end in the casing surface of the connection piece. The connection piece is surrounded by a tubular threaded pipe provided to receive a regulation nut. The threaded pipe is divided into segments by dividing joints which run axially downwardly. The number of segments corresponds to the the number of longitudinal grooves. The grooves are constructed so as to be made radially elastic. The segments are provided with a regulating knob lying radially opposite a longitudinal groove. Each of these segments is able to be brought into operative connection with an inner taper situated on the regulating nut.

The advantages which are able to be achieved thereby consist in particular in that the regulating arrangement can be manufactured in one piece with the lower part of the drip chamber and preparation can take place simply by pushing the tube line on the tubular connection piece and applying the regulating nut.

Particular sensitivity of adjustment can be achieved in that the thread guiding the regulating nut on the pipe is merely arranged on the casing surface of the segments which are not provided with a regulating knob. Further the longitudinal grooves have a cross-section which widens outwards into a V-shape.

Advantageously, the regulating nut can be made undetachable in that the threaded pipe and/or the regulating nut are provided with means which prevent the unscrewing of the latter, or at least make this difficult.

BRIEF DESCRIPTION OF THE DRAWINGS

The regulating arrangement according to the invention is explained in reference to the embodiment illustrated in the drawing, in which.

DESCRIPTION OF THE PREFERRED EMBODIMENT

Figure 1:
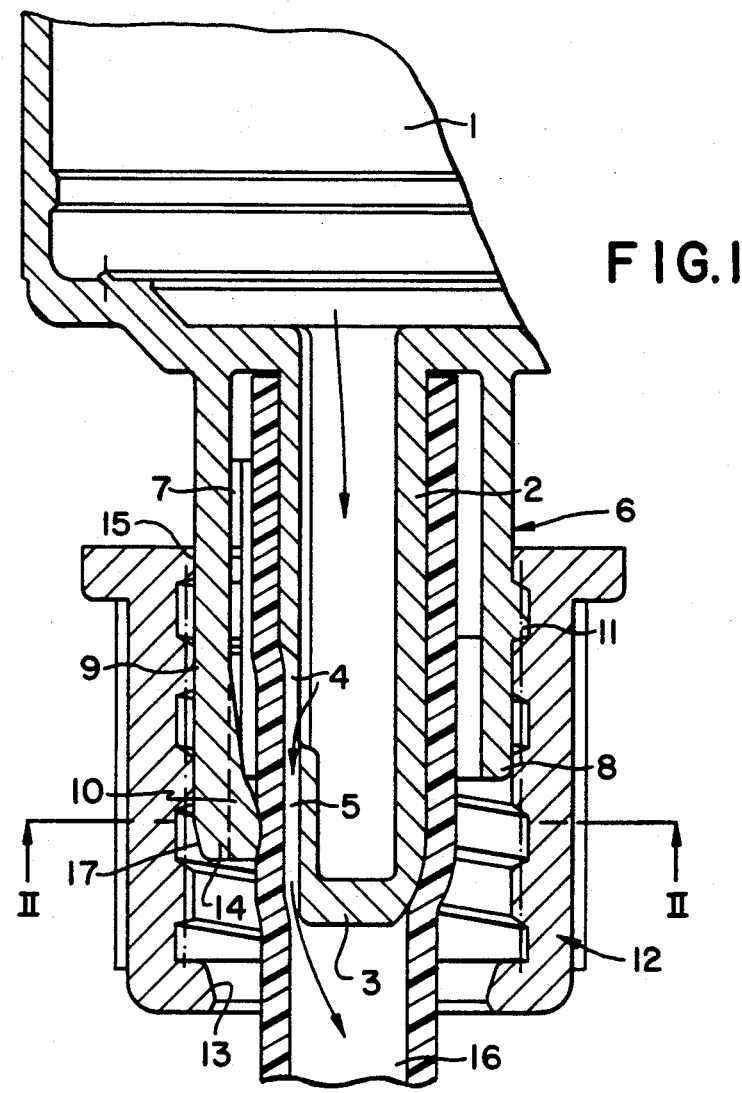
FIG. 1 shows a longitudinal section along line I—I through the lower part of a device constructed according to the invention.
Figure 2:
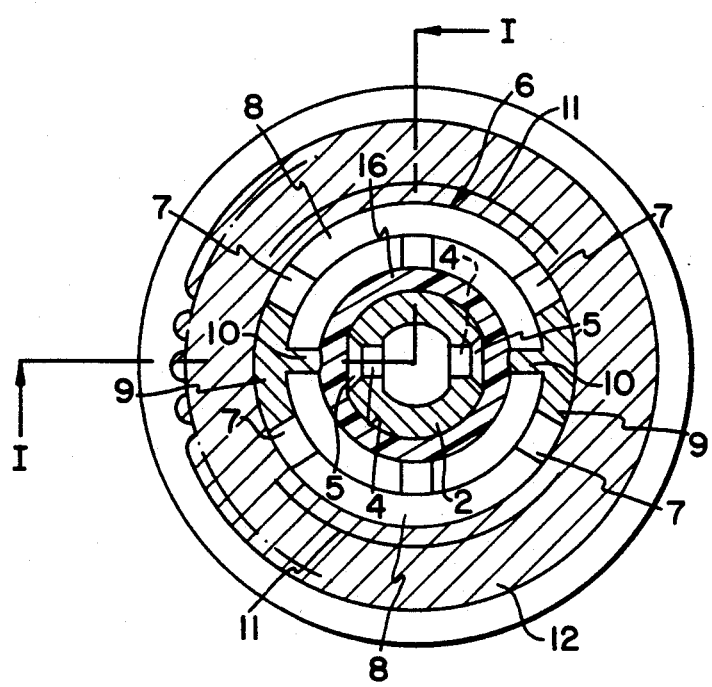
FIG. 2 shows a cross-section along line II—II of FIG. 1.

As can be seen in particular from FIG. 1, a drip chamber 1, which is only partially shown, is provided at its lower end with a tubular connection piece 2, which is constructed so as to be closed at its lower front end 3. The connection piece 2 has at least one lateral perforation 4. FIG. 2 shows here two perforations lying opposite each other, which perforations open out in each case into a longitudinal groove 5 of V-shaped cross-section which is open towards the front end 3, and which grooves are arranged in the casing surface of the connection piece 2. The connection piece 2 is surrounded at a radial distance by a tubular threaded pipe 6, which is divided into segments 8 and 9 by dividing joints 7 which run axially (see FIG. 2). The division is selected such that in each case a segment 9 lies opposite a longitudinal groove 5. These segments 9 are provided in each case with a regulating knob 10 which in each case lies radially opposite a longitudinal groove 5. The thread 11 of the threaded pipe 6 is preferably interrupted in the region of the segments 9 so that the segments 9 are not threaded. The threaded pipe 6 serves to receive a regulating nut 12 which has an inner taper 13 which can come into contact with a circular chamfer 17 of the front end 14 of the segments 9.

The functions of the apparatus described above are as follows:

On assembly of the lower part of the drip chamber with the regulating nut 12, the regulating nut is pressed on such that the inner bead 15 of the nut 12 responsible for undetachability snaps over the thread segment 8. Hence the regulating nut is in the desired position before the assembly of an infusion tube. In this position, the maximum through flow speed of the infusion solution is reached. In this position of the regulating nut 12, a tube line 16 is pushed through the latter onto the connection piece 2. The tube line 16 pushed onto the piece 2 covers the longitudinal grooves 5 without, however, obstructing their cross-section. Hence, the device can now be used. The regulating of the through flow quantity through the tube line takes place by screwing the regulating nut 12 onto the threaded pipe 6, which causes the front ends 14 of the segments 9 to enter into the inner taper 13 of the nut 12 and consequently be deflected radially inwards. Thereby, the regulating knobs 10 situated on these segments 9 draw near to the outer side of the tube line 16 and finally press the latter into the longitudinal grooves 5 situated under the regulating knobs 10. This process may be continued until the cross-section of the longitudinal grooves 5 is completely filled by the material, of the tube 16 so that a narrowing of the through flow cross-section of the groove 5 can take place up to a complete closure of the tube line. For an improved fit of the front ends 14 of the segments 9 into the inner tape 13 of the nut, the segments 9 may be provided in their end regions with the circular chamfer 17.

I claim:

1. A device which is able to be used as a medical infusion or transfusion instrument, comprising a drip chamber for receiving a fluid, a hollow connection piece for supporting a tube line, said hollow connection piece being in fluid communication with said drip chamber, said connection piece extending from a bottom of said drip chamber, and means for regulating the quantity of fluid flowing through the tube line as a fixed component of the drip chamber, characterized in that the connection piece is provided with a closed end and is equipped with at least one radial perforation which opens out into a longitudinally formed groove in a casing surface of the connection piece, said groove extending towards said closed end, a tubular threaded pipe, extending from the bottom of said drip chamber, surrounds said connection piece and has one end for receiving a threaded regulating nut having internal threading, said tubular threaded pipe is divided into segments by joints which run axially, the number of segments corresponding to the number of longitudinal grooves, said segment is radially elastic for movement toward said groove, said segment having ar regulating knob at its free end, the regulating knob lying radially opposite said longitudinal groove, said regulating means further comprising a threaded regulating nut being axially movable along said tubular threaded pipe and having an inner taper situated on the regulating nut for applying inward pressure on the segment and regulating knob to constrict flow in said groove.

2. A device according to claim 1, characterized in that the tubular threaded pipe has a thread for guiding the regulating nut on the pipe which thread is not arranged on an outer casing surface of the segments.

3. A device according to claim 1, characterized in that the longitudinal grooves have a cross-section which widens outwards in a V-shape and that the regulating knobs are constructed so as to be able to be moved toward their respective longitudinal groove.

4. A device according to claim 2, characterized in that the regulating means are provided with means which at least make difficult the complete unscrewing of the nut.

5. A device according to claim 2, characterized in that the longitudinal grooves have a cross-section which widens outwards in a V-shape and that the regulating knobs are constructed so as to be moved toward their respective longitudinal groove.

6. A device according to claim 3, characterized in that the regulating means are provided with means which make difficult the complete unscrewing of the nut.

* * * * *